United States Patent
Alcaya et al.

(10) Patent No.: US 10,393,766 B2
(45) Date of Patent: Aug. 27, 2019

(54) WATER MANAGEMENT SYSTEM FOR ANGLE OF ATTACK SENSORS

(71) Applicant: Rosemount Aerospace Inc., Burnsville, MN (US)

(72) Inventors: Carlos Alcaya, Bloomington, MN (US); Alexander N. Reid, St. Louis Park, MN (US); Richard Alan Schwartz, Faribault, MN (US); William B. Krueger, Bloomington, MN (US); Timothy DeAngelo, Edina, MN (US); Kenneth Freeman, Eagan, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 128 days.

(21) Appl. No.: 15/679,824

(22) Filed: Aug. 17, 2017

(65) Prior Publication Data

US 2019/0056424 A1    Feb. 21, 2019

(51) Int. Cl.
*G01P 13/02*    (2006.01)
*G01F 1/684*    (2006.01)
(Continued)

(52) U.S. Cl.
CPC .......... *G01P 13/025* (2013.01); *G01F 1/6842* (2013.01); *G01P 3/62* (2013.01); *B64D 43/00* (2013.01); *G01N 27/07* (2013.01)

(58) Field of Classification Search
None
See application file for complete search history.

(56) References Cited

U.S. PATENT DOCUMENTS

| 3,082,622 | A | 3/1963 | Andrew |
| 3,208,277 | A | 9/1965 | Hays, Jr. |

(Continued)

FOREIGN PATENT DOCUMENTS

| CN | 103410682 A | 11/2013 |
| CN | 106628206 A | 5/2017 |

(Continued)

OTHER PUBLICATIONS

Extended European Search Report for European Patent Application No. 18189469.2, dated Jan. 21, 2019, 7 pages.

(Continued)

*Primary Examiner* — Jill E Culler
(74) *Attorney, Agent, or Firm* — Kinney & Lange, P.A.

(57) ABSTRACT

An angle of attack sensor includes a housing having an open first end and a closed second end, a heated chassis positioned within the open first end of the housing, a mounting plate positioned on the heated chassis adjacent the open first end of the housing such that an internal chamber is formed between the heated chassis and the mounting plate, a transducer compartment between the heated chassis and the closed second end of the housing, and a water management system located adjacent the internal chamber and the transducer compartment. The water management system includes an annular chamber positioned in the internal chamber, a first tube at a first end of the annular chamber, and a second tube at a second end of the annular chamber. The first tube has a hole such that the first tube is in fluid communication with the annular chamber and the internal chamber, and the second tube is in fluid communication with the annular chamber and the transducer compartment.

20 Claims, 4 Drawing Sheets

(51) Int. Cl.
*G01P 3/62* (2006.01)
*B64D 43/00* (2006.01)
*G01N 27/07* (2006.01)

(56) References Cited

U.S. PATENT DOCUMENTS

| | | | |
|---|---|---|---|
| 3,514,997 | A | 6/1970 | Gwathmey et al. |
| 3,534,600 | A | 10/1970 | Eichweber et al. |
| 3,604,259 | A | 9/1971 | Heinsohn et al. |
| 3,665,760 | A | 5/1972 | Pitches et al. |
| 3,882,721 | A | 5/1975 | Neary et al. |
| 4,230,290 | A | 10/1980 | Townsend et al. |
| 4,390,950 | A | 6/1983 | Muller |
| 4,468,961 | A | 9/1984 | Berg |
| 5,062,869 | A | 11/1991 | Hagen |
| 5,115,237 | A | 5/1992 | Greene |
| 5,438,865 | A | 8/1995 | Greene |
| 6,561,006 | B1 | 5/2003 | Roberge et al. |
| 6,845,658 | B2 | 1/2005 | Roberge et al. |
| 6,918,294 | B1 | 7/2005 | Roberge |
| 7,186,951 | B2 | 3/2007 | Zippold et al. |
| 7,401,507 | B2 | 7/2008 | Collot et al. |
| 7,597,018 | B2 | 10/2009 | Braun et al. |
| 8,397,565 | B1 | 3/2013 | Dillon et al. |
| 2003/0115948 | A1 | 6/2003 | Rouse et al. |
| 2004/0188945 | A1 | 9/2004 | Poincet et al. |
| 2004/0261518 | A1 | 12/2004 | Seidel et al. |
| 2011/0208375 | A1 | 8/2011 | Spoerry et al. |
| 2015/0082878 | A1 | 3/2015 | Bigand |
| 2015/0110149 | A1 | 4/2015 | Begin-Drolet et al. |
| 2015/0344137 | A1 | 12/2015 | Bartz et al. |
| 2016/0033356 | A1 | 2/2016 | DeAngelo et al. |
| 2016/0356175 | A1 | 12/2016 | Waddington |
| 2017/0199218 | A1 | 7/2017 | Benning |
| 2018/0079525 | A1 | 3/2018 | Krueger et al. |
| 2018/0136249 | A1* | 5/2018 | Krueger ............... G01P 13/025 |
| 2019/0056425 | A1 | 2/2019 | Reid et al. |
| 2019/0100327 | A1 | 4/2019 | Krueger et al. |

FOREIGN PATENT DOCUMENTS

| | | |
|---|---|---|
| EP | 1980860 A2 | 10/2008 |
| EP | 2950106 A1 | 12/2015 |
| GB | 2039676 A | 8/1980 |

OTHER PUBLICATIONS

Extended European Search Report for European Patent Application No. 18189477.5, dated Jan. 21, 2019, 10 pages.
Extended European Search Report for European Patent Application No. 18189480.9, dated Mar. 6, 2019, 10 pages.

* cited by examiner

WATER MANAGEMENT SYSTEM FOR
ANGLE OF ATTACK SENSORS

BACKGROUND

The present disclosure relates to sensors, and in particular, to angle of attack sensors. Angle of attack sensors are installed on sides of aircraft to measure the angle of ascent or descent of the aircraft. The transducer compartment of an angle of attack sensor holds the transducer and other electronic components of the sensor. For optimum functionality, the transducer compartment is at the same pressure as the outside environment. As a result, water or other fluid from the outside environment can infiltrate the transducer compartment. Such water can cause damage to the electronic components of the sensor.

SUMMARY

An angle of attack sensor includes a housing having an open first end and a closed second end, a heated chassis positioned within the open first end of the housing, a mounting plate positioned on the heated chassis adjacent the open first end of the housing such that an internal chamber is formed between the heated chassis and the mounting plate, a transducer compartment between the heated chassis and the closed second end of the housing, and a water management system located adjacent the internal chamber and the transducer compartment. The water management system includes an annular chamber positioned in the internal chamber, a first tube at a first end of the annular chamber, and a second tube at a second end of the annular chamber. The first tube has a hole such that the first tube is in fluid communication with the annular chamber and the internal chamber, and the second tube is in fluid communication with the annular chamber and the transducer compartment.

DETAILED DESCRIPTION

An angle of attack sensor has a water management system to prevent water from the outside environment from entering the transducer compartment while maintaining constant pressure communication between the transducer compartment and the outside environment. The water management system of the angle of attack sensor is structured such that it functions on both sides of the aircraft.

Figure 1:
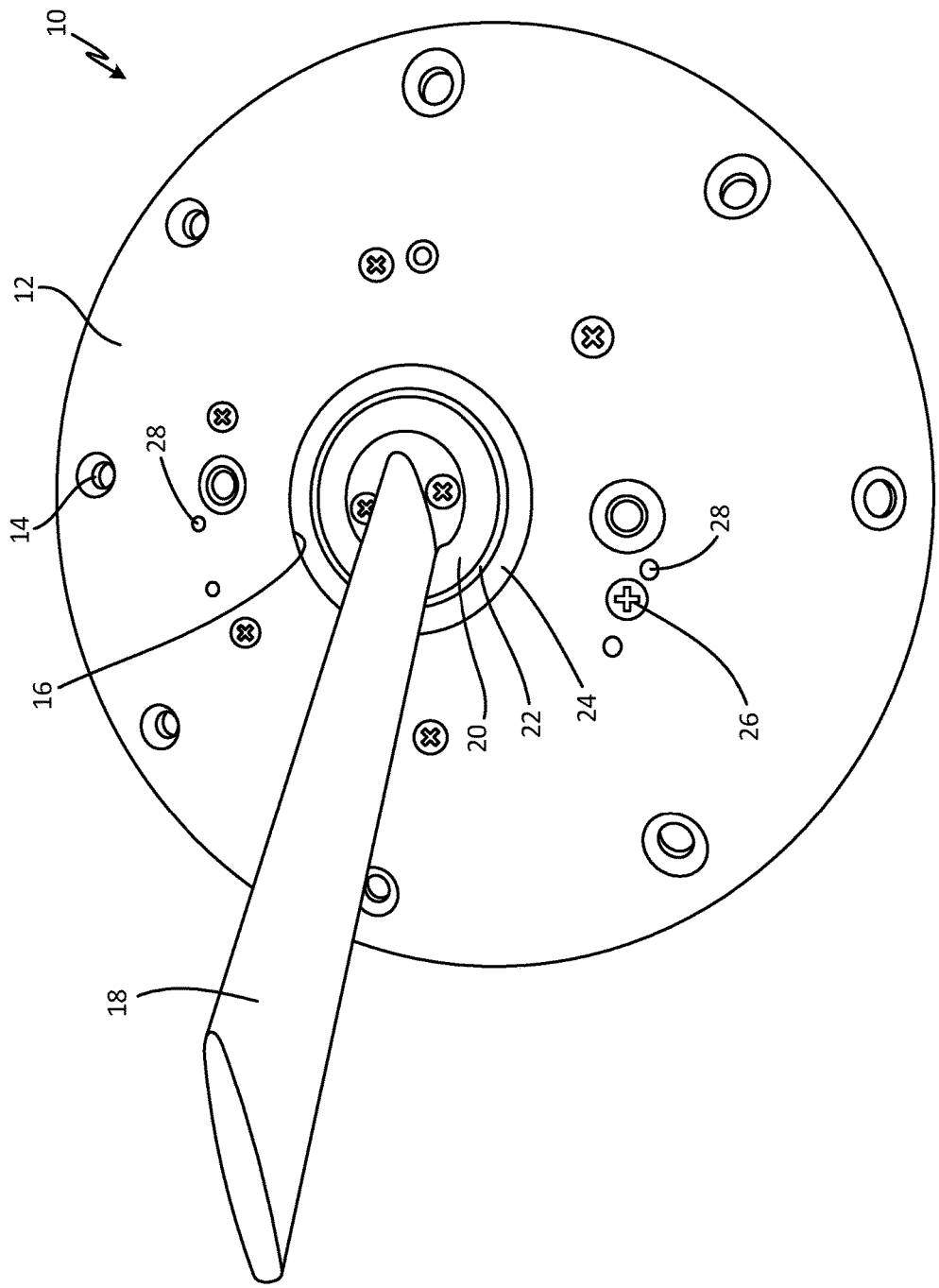
FIG. 1 is a perspective top view of an angle of attack sensor.

FIG. 1 is a perspective top view of angle of attack sensor 10. Angle of attack sensor 10 includes mounting plate 12, mounting holes 14, opening 16, vane 18, slinger 20, void 22, heated chassis 24, fasteners 26, and vent holes 28.

Mounting plate 12 has mounting holes 14 located around a periphery of mounting plate 12. Mounting holes 14 extend through mounting plate 12. In this embodiment, mounting plate has eight mounting holes 14. Mounting plate 12 has circular opening 16 at its center. Vane 18 extends through opening 16 of mounting plate 12. Slinger 20 also extends through opening 16 of mounting plate 12. Vane 18 is attached or mounted to slinger 20. Slinger 20 is a ring around vane 18. Void 22 surrounds slinger 20. A portion of heated chassis 24 also extends through opening 16 of mounting plate 12. Heated chassis 24 surrounds void 22. As such, void 22 acts as a representation of the boundary between parts, such as vane 18 and slinger 20, that rotate and parts, such as heated chassis 24 and mounting plate 12, that do not rotate. Fasteners 26 are positioned around mounting plate 12 interior to mounting holes 14. Fasteners 26 extend through mounting plate 12 into a portion of heated chassis 24 located below mounting plate 12. In this embodiment, six fasteners 26 extend through mounting plate 12. Vent holes 28 are located on mounting plate 12. Vent holes 28 are passageways that extend through mounting plate 12. Mounting plate 12 has four vent holes 28. Vent holes 28 are positioned such that two vent holes 28 are at a first side of mounting plate 12 and two vent holes 28 are at a second side of mounting plate 12.

Angle of attack sensors 10 are installed on the sides of an aircraft and mounted to the aircraft via fasteners such as screws or bolts and mounting holes 14 on mounting plate 12. As a result, mounting plate 12 is about flush with the skin of the aircraft. Vane 18 and slinger 20 rotate with respect to mounting plate 12 and heated chassis 24 via a series of bearings within angle of attack sensor 10. Fasteners 26, such as screws, fasten mounting plate 12 to heated chassis 24. Vent holes 28 enable interior components of angle of attack sensor 10 to be in fluid communication with the outside environment. As such, the pressure inside angle of attack sensor 10 is the same as the pressure of the outside environment. Vane 18 rotates to measure the angle of attack or angle of ascent or descent of the aircraft.

Figure 2:
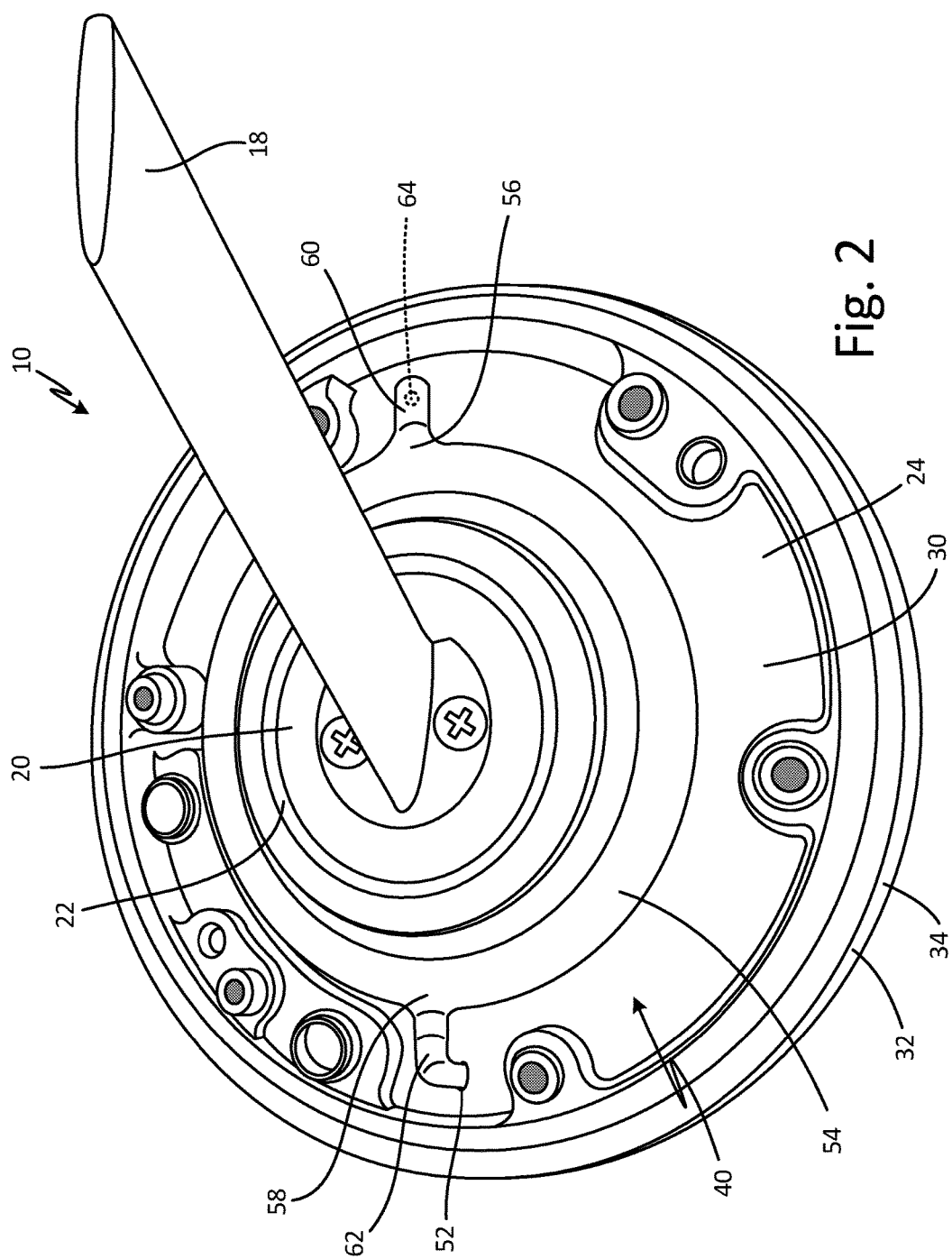
FIG. 2 is a perspective top view of the angle of attack sensor with a mounting plate removed.
Figure 3A:
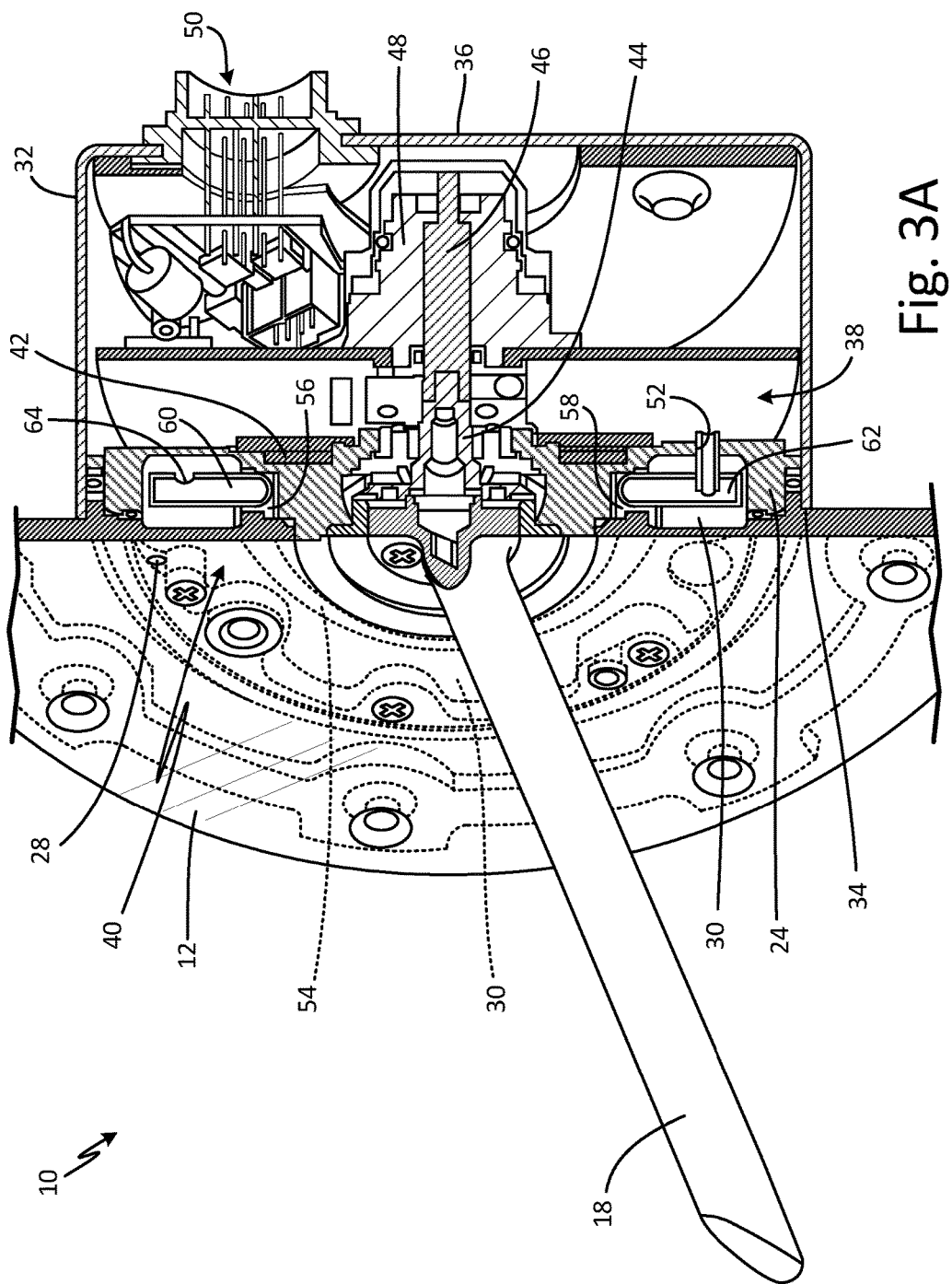
FIG. 3A is an isometric cross-sectional view of the angle of attack sensor in a first position.
Figure 3B:
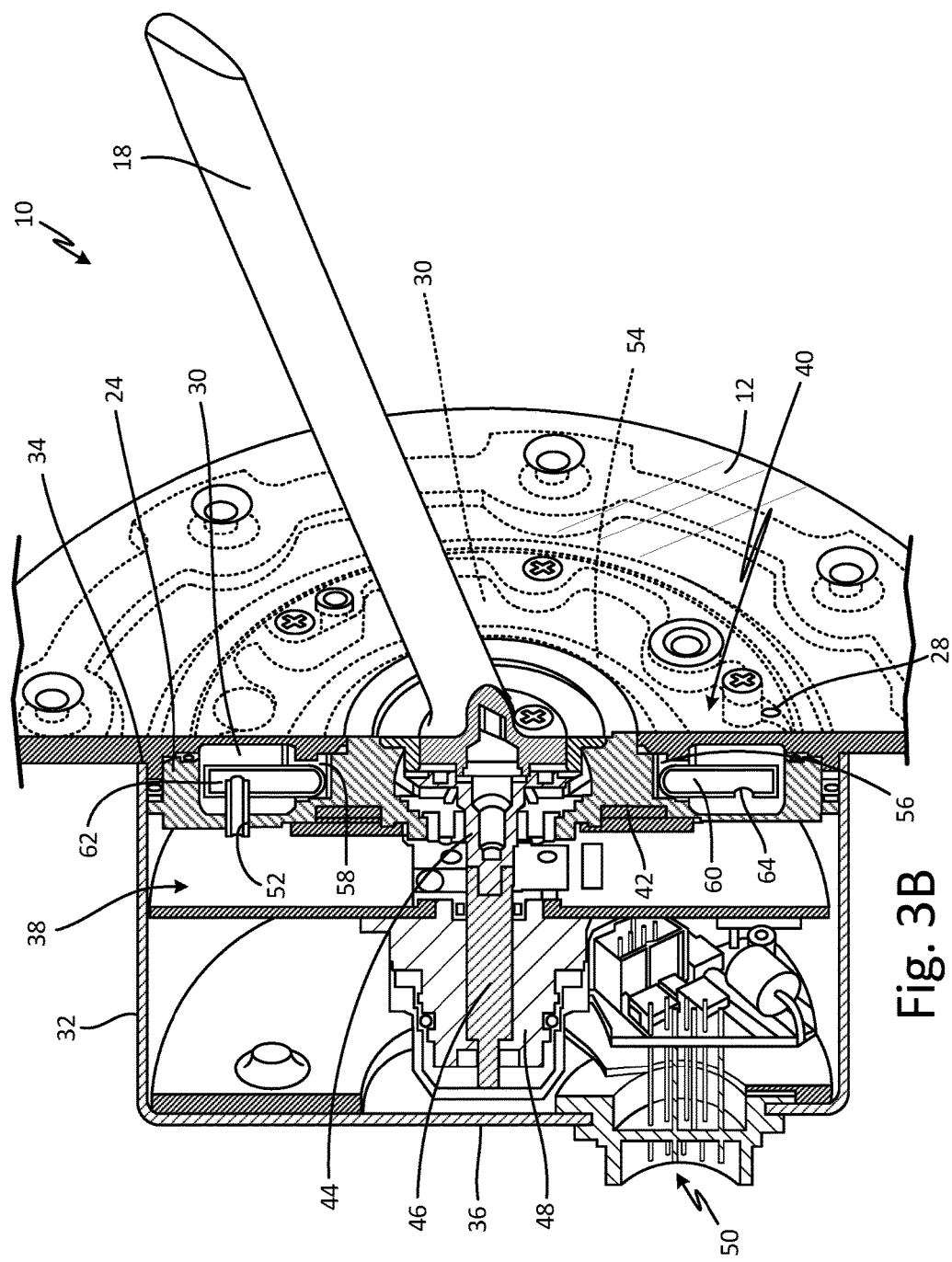
FIG. 3B is an isometric cross-sectional view of the angle of attack sensor in a second position.

FIG. 2 is a perspective top view of angle of attack sensor 10 with mounting plate 12 removed. FIG. 3A is an isometric cross-sectional view of angle of attack sensor 10 in a first position. FIG. 3B is an isometric cross-sectional view of angle of attack sensor 10 in a second position. FIGS. 2, 3A, and 3B will be discussed together. Angle of attack sensor 10 includes mounting plate 12 (shown in FIGS. 3A and 3B), vane 18, heated chassis 24, vent holes 28 (shown in FIGS. 3A and 3B), internal chamber 30, housing 32 having first end 34 and second end 36 (shown in FIGS. 3A and 3B), transducer compartment 38 (shown in FIGS. 3A and 3B), water management system 40, heater 42 (shown in FIGS. 3A and 3B), vane shaft 44 (shown in FIGS. 3A and 3B), transducer shaft 46 (shown in FIGS. 3A and 3B), transducer 48 (shown in FIGS. 3A and 3B), and electronics 50 (shown in FIGS. 3A and 3B). Heated chassis 24 includes passageway 52. Water management system 40 includes annular chamber 54 having first end 56 and second end 58, first tube 60, and second tube 62. First tube 60 includes hole 64.

Mounting plate 12 positioned around vane 18 and fastened to heated chassis 24 has vent holes 28 extending through mounting plate 12, as discussed in reference to FIG. 1. As a result, internal chamber 30, or mounting plate cavity, is formed between heated chassis 24 and mounting plate 12. Vent holes 28 are in fluid communication with internal chamber 30. Vent holes 28 are positioned such that two vent holes 28 are at a bottom of internal chamber 30 regardless of whether angle of attack sensor 10 is in a first position, as shown in FIG. 3A, or a second position, as shown in FIG. 3B. Heated chassis 24 is adjacent housing 32. Housing 32 is cylindrical with an annular sidewall between open first end 34 and closed second end 36. Heated chassis 24 is positioned within open first end 34 of housing 32 such that heated chassis 24 seals open first end 34 of housing 32. As such, mounting plate 12 is adjacent open first end 34 of housing 32 and internal chamber 30 is adjacent open first end 34 of housing 32. Transducer compartment 38 is formed between heated chassis 24 and closed second end 36 of housing 32. Water management system 40 is located adjacent internal chamber 30 and transducer compartment 38. Heater 42 is positioned on heated chassis 24 adjacent transducer compartment 38. Heater 42 is annular, extending all the way around an end of heated chassis 24. A first end of vane shaft 44 is connected to vane 18 and a second end of vane shaft 44 extends through heated chassis 24 into transducer compartment 38. The second end of vane shaft 44 is connected to transducer shaft 46. Transducer shaft 46 is connected to transducer 48 in transducer compartment 38. Electronics 50 are positioned within transducer compartment 38 adjacent transducer 48 and second end 36 of housing 32. Electronics 50 may include circuit boards, electrical connectors, and other electronic equipment.

Passageway 52 extends through heated chassis 24. Passageway 52 extends from internal chamber 30 through heated chassis 24 to transducer compartment 38. Water management system 40 has annular chamber 54 positioned on heated chassis 24 in internal chamber 30. Annular chamber 54 may be a metal tube, such as copper. Annular chamber 34 may be attached to heated chassis 24 via welding, soldering, brazing, embossing, or using any other suitable method of attachment. In alternate embodiments, annular chamber 54 may be machined into heated chassis 24. Annular chamber 54 is circular and extends all the way around internal chamber 30. Annular chamber 54 has first end 56 and second end 58. First end 56 and second end 58 are 180 degrees apart from each other.

First tube 60 is connected to first end 56 of annular chamber 54 and second tube 62 is connected to second end 58 of annular chamber 54. As such, first tube 60 and second tube 62 are both positioned in internal chamber 30. Further, first tube 60 and second tube 62 are at opposite ends of internal chamber 30 such that, in both the first position and the second position, one is at an extreme top of internal chamber 30 and one is at an extreme bottom of internal chamber 30. First tube 60 is in fluid communication with annular chamber 54. First tube 60 is straight and extends away from annular chamber 54. First tube 60 is closed at an end not connected to annular chamber 54. First tube 60 may be a metal tube, such as copper. Second tube 62 is in fluid communication with annular chamber 54. Second tube 62 is not in fluid communication with internal chamber 30. Second tube 62 extends away from annular chamber 54. Second tube 62 extends through passageway 52 in heated chassis 24. Second tube 62 and passageway 52 are sealed together, ensuring that internal chamber 30 is not in fluid communication with passageway 52. As a result, the end of second tube 62 not connected to annular chamber 54 is positioned in transducer compartment 38. Second tube 62 is open at the end not connected to annular chamber 54. Thus, second tube 62 is also in fluid communication with transducer compartment 38. Second tube 62 may be a metal tube, such as copper. In this embodiment, second tube 62 is L-shaped. In alternate embodiments, second tube 62 may be any shape suitable for extending into internal chamber 30 and through passageway 52. Annular chamber 54, first tube 60, and second tube 62 may be unitary. First tube 60 has hole 64. Hole 64 extends through first tube 60 such that first tube 60 is also in fluid communication with internal chamber 30.

Heater 42 heats heated chassis 24, keeping ice out and preventing vane 18 from freezing in place. As such, vane 18 is kept free to rotate. Electronics 50 power heater 42. Electronics 50 also power transducer 48. Transducer 48 acts as a motor. Transducer 48 also measures rotation of transducer shaft 46, and thus vane shaft 44, to produce angle of attack readings.

FIG. 3A illustrates angle of attack sensor 10 in a first position where first tube 60 of water management system 40 is on top. The first position illustrates the position of angle of attack sensor 10 when mounted on the left side of an aircraft. Water or other fluid may enter internal chamber 30 through vent holes 28. Due to gravity, water moves or falls to the bottom of internal chamber 30 where it can drain out of the two vent holes 28 positioned near the bottom of internal chamber 30. If water is entering vent holes 28 at a higher rate than water can exit vent holes 28 near the bottom of internal chamber 30, water pools at the bottom of internal chamber 30. As water accumulates in internal chamber 30, the water level in internal chamber 30 rises. The water in internal chamber 30 will rise and fall as water is gained and drained, respectively. Water at the bottom of internal chamber 30 cannot access second tube 62, and thus cannot access annular chamber 54, as second tube 62 is not in fluid communication with internal chamber 30. Water pools around the exterior of second tube 62. If the water level works its way up internal chamber 30 such that it reaches the top of internal chamber 30, water may enter first tube 60 via hole 64. Due to gravity, water that enters first tube 60 travels through annular chamber 54 until it reaches the bottom of annular chamber 54. Once at the bottom of annular chamber 54, water enters second tube 62 where it can then enter transducer compartment 38. As such, water only has access to transducer compartment 30 by going through water management system 40, and water has to travel 180 degrees up to gain such access. At the same time, air is able to flow into and out of transducer compartment 38, enabling angle of attack sensor 10 to be at the same pressure as the outside environment.

FIG. 3B illustrates angle of attack sensor 10 in a second position where second tube 62 of water management system 40 is on top. The second position illustrates the position of angle of attack sensor 10 when mounted on the right side of an aircraft. Water or other fluid may enter internal chamber 30 through vent holes 28. Due to gravity, water moves or falls to the bottom of internal chamber 30 where it can drain out of the two vent holes 28 positioned near the bottom of internal chamber 30. As stated above, if water is entering vent holes 28 at a higher rate than water can exit vent holes 28 near the bottom of internal chamber 30, water pools at the bottom of internal chamber 30. The water in internal chamber 30 will rise and fall as water is gained and drained, respectively. At the bottom of internal chamber 30, water can enter first tube 60 via hole 64. As water accumulates in internal chamber 30, water also accumulates in annular chamber 54, the water level in internal chamber 30 being about equal to the water level in annular chamber 54. If the water level works its way up such that it reaches the second tube 62, water can then enter transducer compartment 38 through tube 62. As such, water only has access to transducer compartment 30 by going through water management system 40, and water has to travel 180 degrees up to gain such access. At the same time, air is able to flow into and out of transducer compartment 38, enabling angle of attack sensor 10 to be at the same pressure as the outside environment.

Internal chamber 30 acts as a reservoir, collecting water that gets in through vent holes 28. As such, a large volume of water must accumulate in internal chamber 30 or both internal chamber 30 and annular chamber 54 before water has access to transducer compartment 38. Water does not immediately gain access to transducer compartment 38. Therefore, water management system 40 enables angle of attack sensor 10 to be in fluid communication with the outside environment while preventing, or at least decreasing, water ingestion inside the transducer compartment, where water can damage electronics 50. Angle of attack sensor 10 requires fluid communication with the outside environment to maintain optimum performance. Fluid communication with the outside environment reduces contaminated air inside angle of attack sensor 10 and maintains appropriate levels of pressure. Additionally, water management system 40 functions such that angle of attack sensor 10 can be mounted on the left side and the right side of the aircraft, enabling use of angle of attack sensor 10 on both sides of the aircraft. Use of one part for both sides of the aircraft allows for easier manufacture, sales, and installation of angle of attack sensor 10.

Discussion of Possible Embodiments

The following are non-exclusive descriptions of possible embodiments of the present disclosure.

An angle of attack sensor includes a housing having an open first end and a closed second end; a heated chassis positioned within the open first end of the housing; a mounting plate positioned on the heated chassis adjacent the open first end of the housing such that an internal chamber is formed between the heated chassis and the mounting plate; a transducer compartment between the heated chassis and the closed second end of the housing; and a water management system located adjacent the internal chamber and the transducer compartment, the water management system including: an annular chamber positioned in the internal chamber; a first tube at a first end of the annular chamber, the first tube having a hole such that the first tube is in fluid communication with the annular chamber and the internal chamber; and a second tube at a second end of the annular chamber, the second tube being in fluid communication with the annular chamber and the transducer compartment.

The angle of attack sensor of the preceding paragraph can optionally include, additionally and/or alternatively, any one or more of the following features, configurations and/or additional components:

A vent hole is located in the mounting plate.

The vent hole is in fluid communication with the internal chamber.

Four vent holes are located in the mounting plate, with two vent holes being positioned near a bottom of the internal chamber.

A passageway in the heated chassis extends from the internal chamber to the transducer compartment, and the second tube is positioned and sealed in the passageway.

The second tube is L-shaped.

The first end of the annular chamber is positioned 180 degrees from the second end of the annular chamber.

The annular chamber, the first tube, and the second tube are unitary.

The annular chamber is a circular metal tube.

The water management system is metal.

The water management system is copper.

The first tube is not in fluid communication with the transducer compartment.

The second tube is not in fluid communication with the internal chamber.

The heated chassis is positioned in the open first end of the housing such that the first end of the housing is sealed.

The end of the second tube not connected to the annular chamber is open.

A heater is connected to the heated chassis adjacent the transducer compartment; a vane extends through an opening in the mounting plate; a vane shaft is connected to the vane and extends through the heated chassis and into the transducer compartment; a transducer shaft is connected to the vane shaft and a transducer located within the transducer compartment; and electronics are located within the transducer compartment.

The annular chamber is attached to heated chassis using a method selected from the group consisting of: welding, soldering, brazing, and embossing.

The angle of attack sensor is configured to be installed in a first position or a second position, the first tube being at an extreme top of internal chamber in the first position and the second tube being at an extreme top of internal chamber in the second position.

The angle of attack sensor is configured to be mounted on a left side or a right side of an aircraft.

The transducer compartment is in constant pressure communication with an outside environment.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. An angle of attack sensor comprising:
   a housing having an open first end and a closed second end;
   a heated chassis positioned within the open first end of the housing;
   a mounting plate positioned on the heated chassis adjacent the open first end of the housing such that an internal chamber is formed between the heated chassis and the mounting plate;
   a transducer compartment between the heated chassis and the closed second end of the housing; and
   a water management system located adjacent the internal chamber and the transducer compartment, the water management system including:
     an annular chamber positioned in the internal chamber;
     a first tube at a first end of the annular chamber, the first tube having a hole such that the first tube is in fluid communication with the annular chamber and the internal chamber; and
     a second tube at a second end of the annular chamber, the second tube being in fluid communication with the annular chamber and the transducer compartment.

2. The angle of attack sensor of claim 1 and further comprising a vent hole in the mounting plate.

3. The angle of attack sensor of claim 2 wherein the vent hole is in fluid communication with the internal chamber.

4. The angle of attack sensor of claim 2 and further comprising four vent holes in the mounting plate, two vent holes being positioned near a bottom of the internal chamber.

5. The angle of attack sensor of claim 1 and further comprising a passageway in the heated chassis extending from the internal chamber to the transducer compartment, the second tube being positioned and sealed in the passageway.

6. The angle of attack sensor of claim 1 wherein the second tube is L-shaped.

7. The angle of attack sensor of claim 1 wherein the first end of the annular chamber is positioned 180 degrees from the second end of the annular chamber.

8. The angle of attack sensor of claim 1 wherein the annular chamber, the first tube, and the second tube are unitary.

9. The angle of attack sensor of claim 1 wherein the annular chamber is a circular metal tube.

10. The angle of attack sensor of claim 1 wherein the water management system is metal.

11. The angle of attack sensor of claim 10 wherein the water management system is copper.

12. The angle of attack sensor of claim 1 wherein the first tube is not in fluid communication with the transducer compartment.

13. The angle of attack sensor of claim 1 wherein the second tube is not in fluid communication with the internal chamber.

14. The angle of attack sensor of claim 1 wherein the heated chassis is positioned in the open first end of the housing such that the first end of the housing is sealed.

15. The angle of attack sensor of claim 1 wherein the end of the second tube not connected to the annular chamber is open.

16. The angle of attack sensor of claim 1 and further including:
    a heater connected to the heated chassis adjacent the transducer compartment;
    a vane extending through an opening in the mounting plate;
    a vane shaft connected to the vane and extending through the heated chassis and into the transducer compartment;
    a transducer shaft connected to the vane shaft and a transducer located within the transducer compartment; and
    electronics located within the transducer compartment.

17. The angle of attack sensor of claim 1 wherein the annular chamber is attached to heated chassis using a method selected from the group consisting of: welding, soldering, brazing, and embossing.

18. The angle of attack sensor of claim 1 wherein the angle of attack sensor is configured to be installed in a first position or a second position, the first tube being at an extreme top of internal chamber in the first position and the second tube being at an extreme top of internal chamber in the second position.

19. The angle of attack sensor of claim 1 wherein the angle of attack sensor is configured to be mounted on a left side or a right side of an aircraft.

20. The angle of attack sensor of claim 1 wherein the transducer compartment is in constant pressure communication with an outside environment.

* * * * *